(12) United States Patent
Cadieux, Jr. et al.

(10) Patent No.: US 6,373,520 B1
(45) Date of Patent: Apr. 16, 2002

(54) SYSTEM AND METHOD FOR VISUALLY INSPECTING A CIGARETTE PACKAGING PROCESS

(75) Inventors: Edmond J. Cadieux, Jr.; Michael C. Cecil, both of Mechanicsville; H. Coleman Goodman, Jr., Midlothian; Linwood H. Carneal, Richmond, all of VA (US); Gary Kocken, Wrightstown, WI (US); Gregory Russ, Raleigh, NC (US)

(73) Assignee: Philip Morris Incorporated, Richmond, VA (US)

( * ) Notice: Subject to any disclaimer, the term of this patent is extended or adjusted under 35 U.S.C. 154(b) by 0 days.

(21) Appl. No.: 09/549,569

(22) Filed: Apr. 14, 2000

(51) Int. Cl.$^7$ ................................................ H04N 7/18
(52) U.S. Cl. ........................... 348/86; 348/87; 348/125
(58) Field of Search ...................... 348/85–94, 125–130; 53/53, 54, 466

(56) References Cited

U.S. PATENT DOCUMENTS

| | | |
|---|---|---|
| 4,053,056 A | 10/1977 | Day |
| 4,166,973 A | 9/1979 | Lilly, Jr. et al. |
| 4,530,199 A | 7/1985 | Manservisi et al. |
| 4,972,494 A | 11/1990 | White et al. |
| 5,101,609 A | 4/1992 | Cook |
| 5,353,356 A * | 10/1994 | Waugh et al. .................. 382/2 |
| 5,383,322 A * | 1/1995 | Collins, Jr. et al. .............. 53/53 |
| 5,684,530 A * | 11/1997 | White .......................... 348/131 |
| 5,803,702 A * | 9/1998 | Mullins et al. ........... 414/788.7 |
| 5,877,506 A | 3/1999 | Focke et al. |
| 5,970,682 A | 10/1999 | Focke et al. |
| 6,158,193 A * | 12/2000 | Focke et al. .................... 53/53 |

OTHER PUBLICATIONS

Notification of Transmittal of International Search Report or the Declaration dated Sep. 28, 2001 for PCT/US01/12030, International Filing Date Apr. 13, 2001 Priority Date Apr. 14, 2000.

* cited by examiner

*Primary Examiner*—Andy Rao
(74) *Attorney, Agent, or Firm*—Burns, Doane, Swecker & Mathis, LLP

(57) ABSTRACT

A system and method for detecting non-conforming packages such as cigarette packages during travel along a conveyor path. A foil detector can be used to detect a non-conforming foil condition of the packages and a vision inspection system can be used to detect a non-conforming surface feature of the package. The foil detector and vision inspection system can be located at a single inspection station and non-conforming packages can be removed at an ejection station. The ejection station can include a first ejection mechanism such as an air jet for removing packages having a non-conforming foil condition and a second ejection mechanism such as another air jet can be used to remove a package having a non-conforming surface feature. The vision inspection system can include a plurality of video cameras and a reflector which illuminates the package to be inspected with diffused light. The reflector can surround the package undergoing inspection and baffles can be arranged within the reflector housing to prevent hot spots from appearing in the images recorded by the cameras. Using three cameras, one camera can view a surface of the package facing away from the conveyor belt, a second camera can be used to view the top and one side of the package, and the third camera can be used to view the bottom and the other side of the package.

38 Claims, 2 Drawing Sheets

SYSTEM AND METHOD FOR VISUALLY INSPECTING A CIGARETTE PACKAGING PROCESS

BACKGROUND

The present invention relates generally to packaging machines and, more particularly, to a system and method for visually inspecting cigarette packages during the fabrication process.

In cigarette manufacturing, quality control has become a matter of increasing attention. Poor packaging (i.e., packaging which does not conform with predetermined quality requirements) detracts from consumer perceptions of the quality of the packaged goods. Perfectly good items are routinely returned for refund and disposal if they are poorly packaged. On-line inspection during manufacture is one way of controlling packaging non-conformities. In an effort to enhance the on-line quality control capabilities of their production machines, many companies have turned to machine vision techniques wherein cameras are used to allow for inspection of the production process.

U.S. Pat. No. 5,101,609, issued to Cook, discloses a vision inspection system in which a cigarette packaging machine is modified to include an inspection indexing wheel. The inspection indexing wheel is positioned at a post-construction location along the manufacturing process at which the cigarette packages have already been fully constructed.

There exists a need for inspection systems offering ease of setup, reduction in conveyor space, and more reliable inspection of packages such as cigarette packages.

SUMMARY OF THE INVENTION

According to a first embodiment, the invention provides an inspection apparatus for detecting and removing non-conforming packages traveling along a conveyor path, the apparatus comprising a conveyor transporting a plurality of identical packages along a conveyor path, at least one light source illuminating one of the packages at an inspection station along the conveyor path, a first detection device outputting a first signal representing presence of a first non-conforming condition of the package at the inspection station, a second detection device outputting a second signal representing presence of a second non-conforming condition of the package at the inspection station, a first ejection mechanism operable to remove a package having a first non-conforming condition, a second ejection mechanism operable to remove a package having a second non-conforming condition, and a controller operable to process data generated in response to the first and second signals and track packages having the first and/or second non-conforming conditions, the controller being further operable to activate the first and second ejection mechanisms to remove non-conforming packages from the conveyor path.

In accordance with the first embodiment, the first detection device can comprise a foil detection sensor outputting foil signals representing presence of a foil wrapper of the package at the inspection station and the second detection device can comprise at least one camera outputting camera signals representing images of one or more surfaces of the package at the inspection station. In such a case, the first ejection mechanism is operable to remove a package having a non-conforming foil wrapper and the second ejection mechanism is operable to remove a package having a non-conforming image.

In accordance with the first embodiment, the invention provides a method of detecting and removing non-conforming packages traveling along a conveyor path, the method comprising transporting a plurality of identical packages along a conveyor path, operating a first detection device to output a first signal representing a first non-conforming condition of a package at an inspection station along the conveyor path, operating a second detection device to output a second signal representing a second non-conforming condition of a package at the inspection station, operating a controller to track packages having the first and second non-conforming conditions, and operating the controller to activate a first ejection mechanism to remove a package having a first non-conforming condition when the non-conforming package is at an ejection station along the conveyor path, and operating the controller to activate a second ejection mechanism to remove a package having a second non-conforming condition when the non-conforming package is at the ejection station. In a preferred method, the first detection device comprises a foil detection sensor which outputs foil signals representing a foil condition of a foil wrapper of a package at the inspection station and the second detection device comprises at least one camera which outputs camera signals representing at least one surface condition of a package at the inspection station, the method including processing the camera signals and the foil signals to identify a package at the inspection station which contains a non-conforming surface feature or non-conforming foil wrapper.

According to a second embodiment, the invention provides an inspection apparatus for visually detecting non-conforming packages traveling along a conveyor path, the apparatus comprising a conveyor transporting a plurality of identical packages along a conveyor path, a light source illuminating one of the packages at an inspection station along the conveyor path, the light source illuminating the package at the inspection station using a diffuse lighting source which includes a light reflector and at least one fiber optic lighting element, the at least one fiber optic lighting element delivering a pulsed beam of light to the light reflector while a package is located at a camera inspection position, and the light reflector illuminating the package with diffused light reflected from a surface of the light reflector, at least one camera outputting camera signals representing images of one or more surfaces of the package at the inspection station, and a controller operable to process data generated in response to the camera signals and identify a package having a non-conforming surface feature.

According to the second embodiment, the invention additionally provides a method of visually detecting non-conforming packages traveling along a conveyor path, the method comprising transporting a plurality of identical packages along a conveyor path, illuminating one of the packages at an inspection station along the conveyor path, the package being illuminated at the inspection station using a diffuse lighting source which includes a light reflector and at least one fiber optic lighting element, the at least one fiber optic lighting element delivering a pulsed beam of light to the light reflector while a package is located at a camera inspection position, and the light reflector illuminating the package with diffused light reflected from a surface of the light reflector, outputting camera signals representing images of one or more surfaces of the package at the inspection station, and processing data generated in response to the camera signals so as to identify a package having a non-conforming surface feature. According to this method, the package can be illuminated using a plurality of fiber optic elements delivering pulsed beams of light into the reflector, the reflector including a flat white coating on a surface thereof facing the package to be inspected. The reflector can include a housing which surrounds a vertically oriented conveyor belt, the method including using a conveyor belt traveling over a vacuum chamber to apply a vacuum force to the belt to hold a package thereon as it travels through the inspection station.

DETAILED DESCRIPTION OF THE INVENTION

Figure 1:
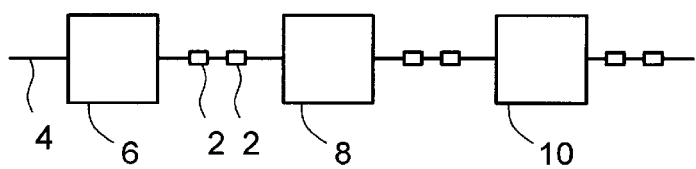
FIG. 1 shows a packaging line in accordance with the invention.

The invention provides an improved inspection system for inspecting packaged articles such as cigarette packs. Further, the inspection system allows rejection of non-conforming packages into one or more discard locations dependent on a detected condition of a package while it travels along a feed path. For instance, a plurality of air jets can be used to remove a non-conforming package by activating one air jet to deflect a non-conforming package into a first location when a first quality inspection device detects a first non-conforming condition and a second air jet can be activated to deflect another non-conforming package into a second location when a second quality inspection device detects a second non-conforming condition. Accordingly, an advantage of the inspection system according to the invention is that a more compact conveyor arrangement can be used to inspect the packages compared to a system in which separate ejection stations are used to inspect and remove non-conforming packages.

According to a first embodiment of the invention, the inspection includes two inspection devices and a single ejection station wherein two air jets are used to remove non-conforming packages at a single location along a conveyor. The air jets can be oriented to deflect non-conforming packages from the conveyor such that packages having a first non-conforming feature are deflected into a first discard location and packages having a second non-conforming feature are deflected into a second discard location. The air jets can be located on opposite sides of the conveyor and oriented at an angle relative to the direction of travel of the conveyor. As an example, the air jets can be oriented at any suitable angle such as, for example, 20 to 80°, preferably 35 to 75° to the direction of travel of the packages. The angle of the jets can be adjusted as desired to accommodate various conveyor speeds. In operation, the conveyor can process 200 to 800, e.g. around 400 packages per minute. The first and second discard locations can comprise reject bins which accumulate the non-conforming packages.

According to a second embodiment of the invention, the inspection station is a vision inspection system which includes a diffuse lighting arrangement which provides indirect lighting of a package as it travels along the conveyor path. A preferred lighting arrangement is a dome and baffle arrangement that surrounds the package in the inspection area. In such an arrangement, light can be brought into four corners of the light dome via fiber optics and the baffles can be used to deflect the light such that the light from the fiber optics does not illuminate the pack without first reflecting off of the dome. The dome preferably includes a "flat" powder coating on interior surfaces thereof which diffuses the light such that the light which is directed onto the package is very diffuse and provides reproducible results when used to inspect packages traveling along the conveyor path. The flat coating can comprise a powder which has been electrostatically attracted to the inner surfaces of a metal dome with or without baffles therein and melted or fused to the inner surfaces of the dome. Preferably, the flat coating is suitable for providing diffuse lighting of various types of graphics used on the exterior of the packages being inspected. Compared to direct lighting inspection systems, the diffuse lighting arrangement according to the invention is more advantageous in terms of ease of set-up and maintenance for various package designs to be inspected, more repeatable lighting, better image quality providing more consistent and accurate inspection of the packages, and/or more adaptable lighting within tolerances of different vision inspection programs.

FIG. 1 is schematic of a packaging line wherein packages 2 travel in single file along a conveyor path 4 from a packaging machine 6 to an inspection station 8 and then an ejection station 10. The packaging machine 6 preferably comprises a cigarette packaging machine wherein cigarettes are packaged in soft or hard pack wrappers. According to a first embodiment of the invention, the packages 2 are inspected at two discrete locations in the inspection station 8 and the ejection station 10 removes non-conforming packages from the conveyor path. According to another embodiment of the invention, the inspection station 8 includes a vision inspection system which utilizes diffuse lighting.

Figure 2:
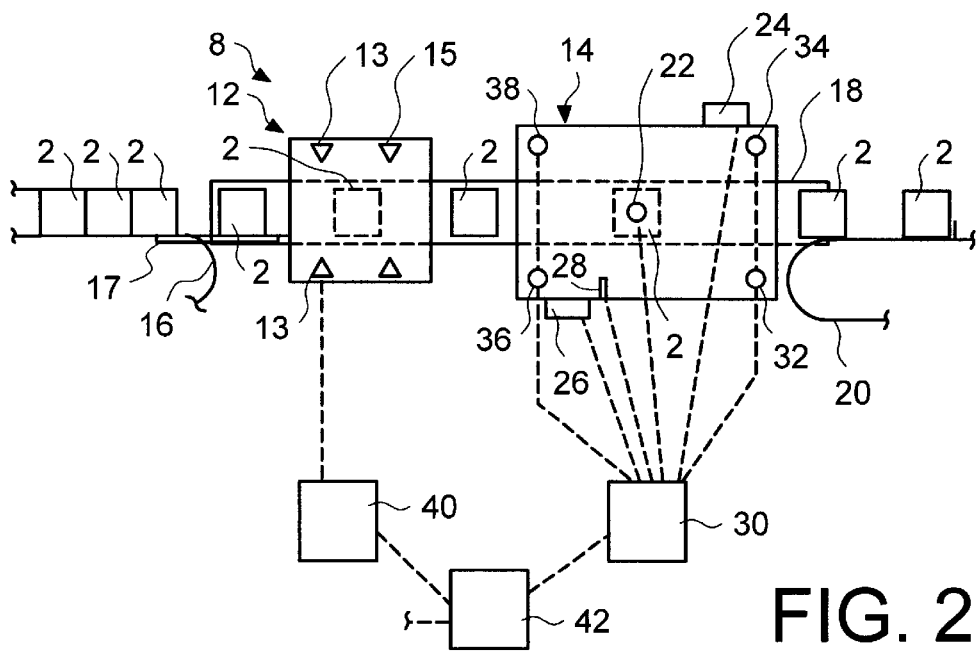
FIG. 2 shows a side view of an inspection station in accordance with one embodiment of the invention.

FIG. 2 illustrates a side view of the inspection station 8 according to the first embodiment of the invention. As shown, the inspection station 8 includes a first inspection device 12 and a second inspection device 14. The packages 2 travel along a first conveyor 16 and are transferred onto a second conveyor belt 18 prior to passing through the first inspection device 12. The speed of belt 18 can be set to speed up the packages and provide a desirable spacing therebetween as they travel on belt 18. Further, a guide rail 17 can be used to provide desired positioning of the packages on the belt 18. After passing through the second inspection device 14 the packages 2 are transferred onto a third conveyor belt 20. Preferably, the ejection station 10 is located close to (e.g., within one meter of) the inspection station 8 such that a package inspected at station 8 can be removed from the conveyor path immediately after the inspection detects a non-conforming feature.

The first inspection device 12 can be a foil detection device which examines four sides of the package 2 to determine the presence or absence of a foil wrapper. For example, the device 12 can include one or more detection sensors distributed around the package 2 as it travels through the inspection device 12. The sensors can be monitored to detect foil from the time a package passes photosensor cell 13 to the time the package passes photosensor cell 15. The second conveyor 18 can be a vertically oriented endless belt having a vacuum arrangement which holds the packages 2 against the belt as the belt travels through the first and second inspection devices 12, 14.

The second inspection device 14 can be a vision inspection system which includes at least one camera which records images of at least one surface of the package 2 as it travels through the second inspection device 14. In a preferred arrangement for inspecting hard pack cigarette packages without clear overwrap films, the second inspection device 14 includes three cameras at locations 22, 24 and 26. The camera at location 22 is oriented to view a front surface of the package 2, the camera at position 24 is oriented to view the top and right side of the package 2, and the camera at location 26 is oriented to view the bottom and left side of the package 2. A photosensor 28 detects the arrival of a package 2 and sends a signal to a controller 30 which in turn activates a light source (such as four fiberoptic bundles 32, 34, 36, 38) which illuminates the package 2 with a flash of light when the package 2 is at a desired viewing position within the inspection device 14. The controller 30 also receives signals from the cameras representing the images viewed by the cameras and the signals are processed by suitable vision inspection software such that non-conforming packages 2 are identified via a signal sent to programmable logic controller (PLC) 42. Likewise, the first detection device 12 outputs signals to suitable circuitry 40 which identifies non-conforming packages 2 and sends signals identifying such non-conforming packages to the controller 42. The controller 42 tracks the non-conforming packages and instructs the ejection station 10 to remove the non-conforming packages from the conveyor path 4.

Figure 3:
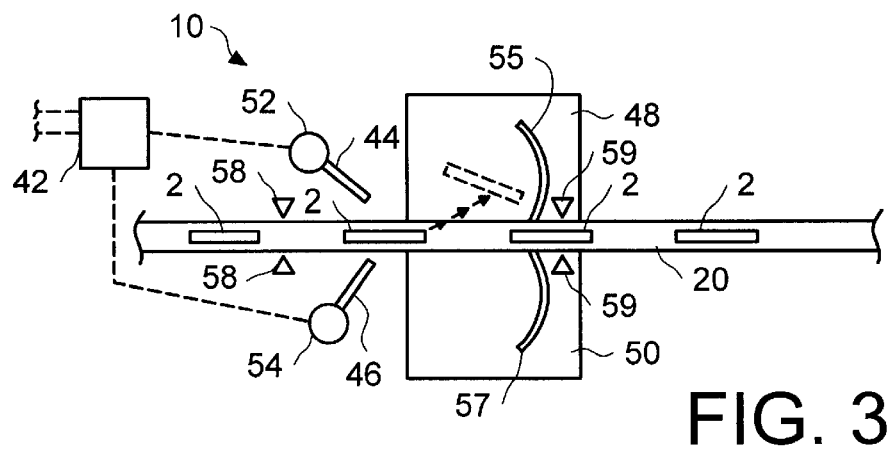
FIG. 3 shows a top view of an ejection station in accordance with an embodiment of the invention.

FIG. 3 illustrates a top view of an embodiment of the ejection station 10 having two ejection mechanisms. As shown, the ejection station 10 includes the third conveyor 20 on which the packages 2 travel in spaced-apart relation and first and second air jets 44, 46 are selectively activated by the controller 42 to remove a non-conforming package 2 from the conveyor 20 into first and second containers 48, 50. In operation, the controller 42 sends a signal which opens a high speed air valve 52 of the air jet 44 to eject a non-conforming package 2 into the container 50 or the controller 42 actuates another high speed valve 54 to operate the air jet 46 to eject a package into the container 48. Such high speed air valves are commercially available, e.g., Part No. 45A-BA1-DEFJ-JM mod. 2474 available from a company called Mac Valve. If desired, deflectors 55, 57 can be arranged to deflect packages into suitable chute arrangements to guide deflected packages into the appropriate container. Further, suitable photocells such as photocells 58, 59 can be used to signal the PLC that a package has arrived at the ejection station 10 and confirm through a timed sequence programming operation that the package has been ejected, i.e., within a preset period the second photocell 59 should not detect a package that has been ejected by one of the air jets. In this way, packages having different non-conforming features can be separated and accumulated in different containers arranged to hold non-conforming articles having the same non-conforming feature.

Figure 4:
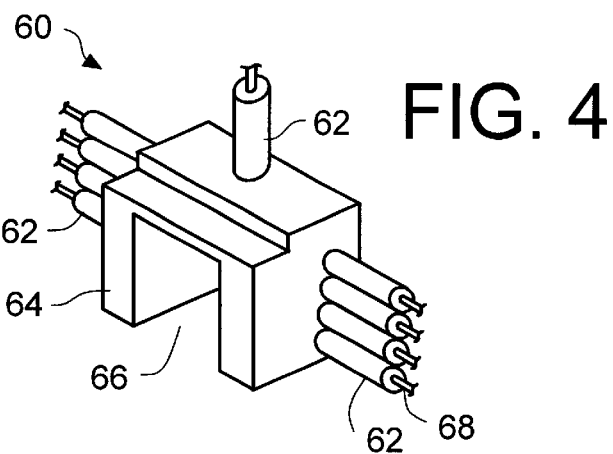
FIG. 4 shows a perspective view of a foil detector which can be used in the inspection station according to the invention.
Figure 5:
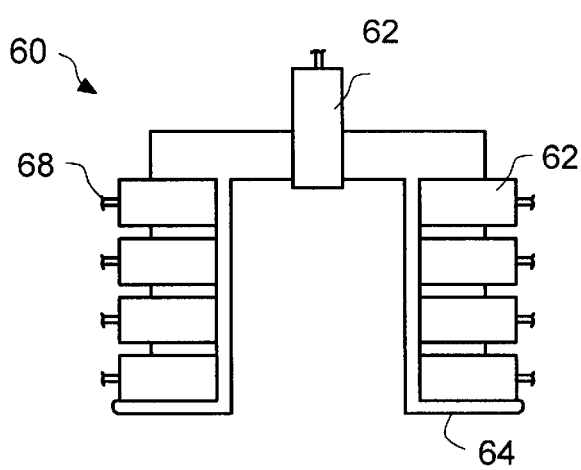
FIG. 5 shows a front view of the foil detector shown in FIG. 4.

FIGS. 4 and 5 show details of a foil inspection device which can be used in the first embodiment of the invention. FIG. 4 shows a perspective view of a top portion of a foil inspection device 60 wherein nine proximity sensors 62 are shown mounted in a housing 64. The sensors 62 are effective for detecting the presence of a foil wrapper on a package traveling through an opening 66 in the housing 64. If one or more of the sensors 62 detects an absence of foil on the package traveling through the opening 66, an appropriate signal is transmitted via a respective electrical lead 68 to the circuit 40. The foil detection device 60 includes a 10th sensor (not shown) in the same plane as the other sensors and oriented similar to the single sensor shown on the upper portion of the housing 64. In the preferred arrangement, the sensors 62 are arranged to detect a foil wrapper of a cigarette package traveling on its side edge such that the long dimension of the cigarette package is parallel to the direction of travel of the package. In this way, one group of four sensors 62 detects the presence of the foil wrapper on the side of a package held against the belt 18, the other group of four sensors 62 detects the presence of the foil wrapper on the opposite side of the cigarette package and the single sensors 62 at the top and bottom of the housing detect the presence of the foil wrapper along the side edges of the cigarette package. The sensors 62 are commercially available, e.g., part No. 3RG46-0GB01 available from Siemens Corporation.

Figure 6:
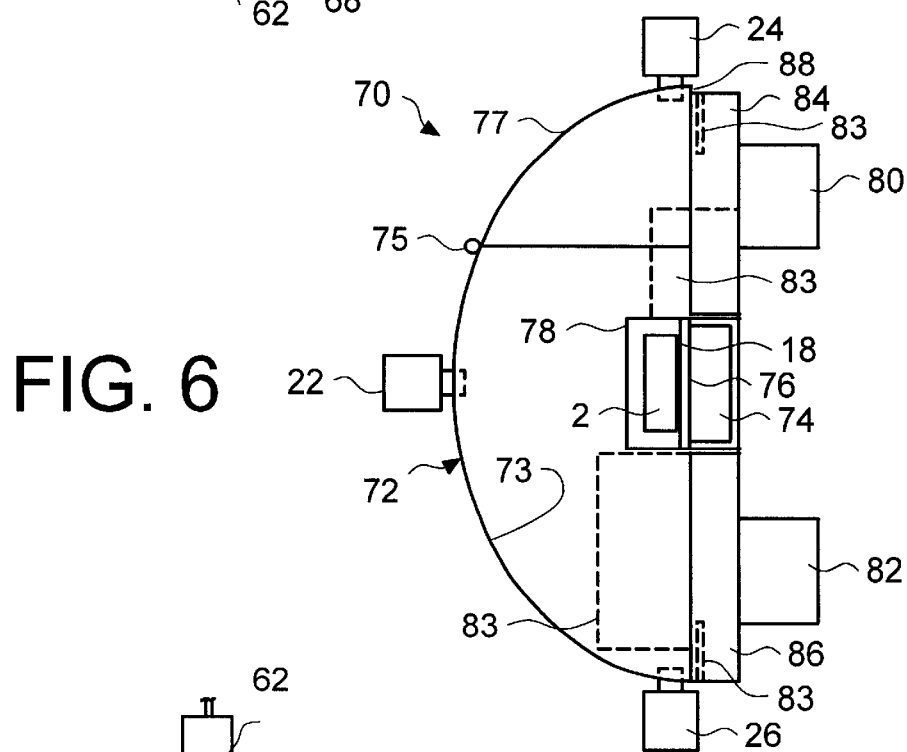
FIG. 6 shows a side cut-away view of a vision inspection device in accordance with an embodiment of the invention.

FIG. 6 shows a side cut-away view of a preferred vision inspection device 70 wherein a package 2 is carried via conveyor belt 18 through a reflector housing 72. The conveyor belt 18 is vertically oriented and passes over a vacuum chamber 74 which applies a vacuum force on the package 2 through a perforated cover plate 76 and the belt 18 which is also air permeable. The packages 2 enter the reflector housing 72 through an opening 78. The reflector housing 72 is illuminated with a light source such as one or more fiberoptic bundles mounted at suitable locations. For example, four fiberoptic bundles can be mounted at corners of the reflector housing by suitable supports, two of which are shown at 80, 82. Further, baffles 83 can be arranged in any suitable arrangement within the reflector housing 72 to deflect the light from the fiberoptic bundles such that hot spots are not formed on the package as it is inspected by cameras at locations 22, 24, 26.

The reflector housing 72 includes a curved portion 73, the inside surface of which is coated with a flat white coating which provides diffused uniform lighting of the package when the light source illuminates the package for viewing by the cameras. The flat white coating is preferably provided on all internal surfaces which reflect light in the housing 72. In order to obtain access to the interior of the reflector housing 72, the curved portion of the housing can be provided in two parts which are hinged together as shown at 75. The hinge 75 allows the upper portion 77 of the housing to rotate counterclockwise and thereby provide access to the interior of the reflector housing 72. The back wall of the reflector housing 72 includes an upper rectangular tray 84 and a lower rectangular tray 86, the upstanding edges of each tray facing the interior of the housing 72. A gap 88 can be provided at the upper portion of the reflector housing 72 for supply of air which can be used to remove dust from the reflector housing through a suitable opening (not shown) at the bottom of the housing.

In operation, the foil detector can be used to scan four sides of a pack as it travels through the foil inspection station 60. The sensors 62 look for voids in the foil wrapper such as tears or missing portions of the foil wrapper while the package travels between photocells 13, 15. If such voids are detected, a signal is sent to a PLC which coordinates with a valve of an ejection mechanism to remove the non-conforming package from the conveyor path at the ejection station. For example, the sensors 62 are monitored as a package passes through the housing 64, and if one or more of the sensors 62 detects one or more imperfections in the foil wrapper, an appropriate signal or signals can be sent to the PLC. The PLC communicates with a controller which tracks the non-conforming package and operates the ejection mechanism to remove the non-conforming package at the ejection station. The conveyor belt 16 is a non-metallic conveyor belt and the four sensors 62 adjacent the conveyor belt 16 sense the presence of a foil wrapper on the side of the package in contact with the conveyor belt 16.

At the vision inspection system, the light source is a strobe arrangement which provides a flash of light when the package is at a desired location. The vision inspection device can include suitable adjustments for timing the flash of the light within a variable distance from the location at which the package is detected by the photosensor 28. The cameras are arranged so that the camera at location 22 views the entire surface of the package on the opposite side of the package held against the conveyor belt 18, the camera at location 24 is arranged to view the top side edge and downstream end edge of the package and the camera at location 26 is oriented to view the bottom side edge and upstream end edge of the package as it travels through the reflector housing 72. Further, the light provided to the reflector housing 72 is dispersed by suitable baffles and reflected from the flat white coating on the interior of the curved surface 73 whereby the package is provided with a consistent and even distribution of diffused light. The flat white coating can be any suitable coating such as the type used on office furniture and preferably is a low gloss coating providing, for example, about 20% reflectance. The combination of the flat white coating on the interior surface of the reflector and the baffles redirects the light provided by the fiberoptic bundles so as to create a consistent illumination field which is especially useful when the lighting arrangement is used from one machine to another. That is, the diffuse lighting arrangement in accordance with the invention greatly simplifies setup from machine to machine and eliminates the need to reprogram data files during such setup procedures. The location and size of the baffles within the reflector housing 72 will depend on the number of cameras used and the viewing angles of such cameras.

In the ejection station the non-conforming packages are removed from the conveyor belt 20 by any suitable arrangement. In the preferred arrangement, air jets are used to knock non-conforming packages into containers arranged to accumulate non-conforming packages having the same type of non-conforming feature. Although the inspection station 8 has been described as including a foil detection device and a vision detection device, other types of inspection devices could be substituted therefor. For instance, the detection devices could be set up to detect other features such as date codes or other features of the packages as they travel along the conveyor path. An advantage of the detection station in accordance with the invention is the savings in conveyor space achieved by combining more than one ejection mechanism at the ejection station it is possible to achieve further savings in conveyor space.

The vision inspection system according to the present invention can be used to identify packaging non-conformities commonly associated with the cigarette packaging process. These non-conformities commonly appear on the cigarette package, which can be either a hard or soft pack cigarette package, for example, such as a tear or hole in the packaging, smearing of ink, spots of foreign matter, missing or misaligned graphics or print, reversed wrapper blank, or other visually detectable feature. One skilled in the art will appreciate that non-conformities can be created in several places during packaging. The vision inspection system of the present invention can utilize a digital camera, such as a PPT Vision DSL Series Camera and a lighting device incorporating fiber optic bundles available from various suppliers such as Fostec. The camera and lighting device can be positioned so as to allow the camera to form electrical signals which, according to a preferred embodiment, represent an image of the outer wrapper subsequent to the packaging process. According to an embodiment of the present invention, the camera captures one or more images of the package and forwards this image (i.e., the formed electrical signals) to a processor. One skilled in the art will appreciate that the digital camera could, in the alternative, capture separate images of sections of the package which are of greatest interest.

When the processor receives the formed electrical signals from the camera, the processor determines, based on these signals, the conformity of the cigarette package. According to a preferred embodiment, the processor receives an image of the package and considers only those sections of the received digital image which represent the objects of interest (e.g., imperfection in the packaging, smearing of ink, spots of foreign matter, missing or misaligned graphics or print, reversed wrapper blank, or other visually detectable feature). For example, the processor can compare the color (i.e., the pixel value) of a section of the digital image to a predetermined pixel value.

If the pixel values of the sections of the viewed images equal the predetermined pixel value, the package is registered as conforming and the next package is inspected. If the pixel value of one or both of the sections of the viewed images does not equal the predetermined pixel value, then this indicates that the wrapper is non-conforming. When it is determined that the wrapper is non-conforming, the processor registers the cigarette package as non-conforming. The processor tracks the cigarette packages by tracking the positions thereof via, for example, assigning a number to the individual cigarette packages. In this manner, the processor can simply store a bit with the assigned number of a non-conforming package indicating that it is such. One skilled in the art will appreciate that many other methods of registering a non-conforming package exist which could alternatively be employed.

When a cigarette package is registered as non-conforming, the processor sends a signal to a PLC which controls the timing of the ejection mechanism indicating that the particular cigarette package is to be rejected off the machine. A fiberoptic sensor arrangement is preferably used to determine if a non-conforming package has entered the ejection station. The registered, non-conforming cigarette package is then rejected at the ejection station which is downstream of the inspection station. The detection and ejection of the cigarette package at this stage of the cigarette assembly process allows for the operator to immediately determine where packaging problems occur in the packaging line due to the separation of packages having foil non-conformities from packages having wrapper non-conformities. Moreover, the information gleaned from the processor comparison aids in diagnosing problems with the cigarette packaging machine. For example, a repeated indication that the wrapper is reversed could indicate that a group of blanks were incorrectly inserted in the feeding hopper. In such an event, the operator could stop the packaging operation and correct the error, thereby circumventing the continued application of the incorrectly inserted blanks to the wrapped bundles of cigarettes. Likewise, other non-conformities such as printing errors, etc., could be readily identified and appropriate corrective action could be taken.

The foregoing has described the principles, preferred embodiments and modes of operation of the present invention. However, the invention should not be construed as being limited to the particular embodiments discussed above. For example, one skilled in the art will appreciate that the implementation of the inspection and ejection stations of the present invention is merely exemplary and that the present invention is equally applicable to other types of packaging machines. For instance, one skilled in the art will appreciate that the present invention is not only applicable to cigarette packaging systems, but is equally applicable to other types of systems where quality is desired in the packaging fabrication process. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. An inspection apparatus for detecting and removing non-conforming packages traveling along a conveyor path, the apparatus comprising:
    a conveyor transporting a plurality of identical packages in a single row along a conveyor path;
    at least one light source illuminating one of the packages at an inspection station along the conveyor path;
    a first detection device outputting a first signal representing presence of a first non-conforming condition of the package at the inspection station;
    a second detection device outputting a second signal representing presence of a second non-conforming condition of the package at the inspection station;
    a first ejection mechanism operable to remove a package having a first non-conforming condition from said single row into a first discard location;
    a second ejection mechanism operable to remove a package having a second non-conforming condition from said single row into a second discard location different than the first discard location; and
    a controller operable to process data generated in response to the first and second signals and track packages having the first and/or second non-conforming conditions, the controller being further operable to activate the first and second ejection mechanisms to remove non-conforming packages from the single row of packages.

2. The apparatus as defined in claim 1, wherein the first detection device comprises a foil detection sensor outputting foil signals representing presence of a foil wrapper of the package at the inspection station and the second detection device comprises at least one camera outputting camera signals representing images of one or more surfaces of the package at the inspection station, the first ejection mechanism being operable to remove a package having a non-conforming foil wrapper and the second ejection mechanism being operable to remove a package having a non-conforming image.

3. The apparatus as defined in claim 1, wherein the first ejection mechanism comprises a first air jet and a first removal bin, the first air jet being oriented to direct an air stream at the package with sufficient force to cause the package to fall into the first removal bin.

4. The apparatus as defined in claim 3, wherein the second ejection mechanism comprises a second air jet and a second removal bin, the second air jet being oriented to direct an air stream at the package with sufficient force to cause the package to fall into the second removal bin.

5. The apparatus as defined in claim 2, wherein the controller includes a computer running a vision inspection program.

6. The apparatus as defined in claim 1, wherein the package is a cigarette package and the first and second detection devices inspect the cigarette for non-conforming packaging features.

7. The apparatus as defined in claim 2, wherein the at least one camera comprises at least one video camera.

8. The apparatus as defined in claim 2, wherein the at least one camera comprises three video cameras oriented to inspect different surfaces of the package.

9. The apparatus as defined in claim 1, wherein the first and second ejection mechanisms are located at an ejection station downstream of the inspection station.

10. The apparatus of claim 2, wherein the foil detection sensor is located upstream from the at least one camera.

11. A method of detecting and removing non-conforming packages traveling along a path, the method comprising:
    transporting a plurality of identical packages along a path;
    generating a first signal indicative of a first non-conforming condition of a package at an inspection station along the path;
    generating a second signal indicative of a second non-conforming condition of a package at the inspection station;
    tracking any packages having the first and second non-conforming conditions;
    activating a first ejection mechanism to remove a package having the first non-conforming condition at an ejection station along the path to a first discard location; and
    activating a second ejection mechanism to remove a package having the second non-conforming condition at the ejection station to a second discard location different than the first location.

12. The method of claim 11, wherein the first signal is indicative of a foil condition of a foil wrapper of a package at the inspection station and the second signal is indicative of at least one surface condition of a package at the inspection station.

13. The method of claim 12, further comprising illuminating the package at the station inspection using a diffuse lighting source which includes a light reflector and at least one fiber optic lighting element, the at least one fiber optic lighting element delivering a pulsed beam of light to the light reflector while a package is located at a camera inspection position, and the light reflector illuminating the package with diffused light reflected from a surface of the light reflector.

14. The method of claim 11, wherein the first ejection mechanism ejects the non-conforming package into a first container.

15. The method as defined in claim 14, wherein the second ejection mechanism ejects the non-conforming package into a second container.

16. The method as defined in claim 11, wherein the first and second ejection mechanisms comprise first and second air jets, the first air jet ejecting a blast of air with sufficient force to deliver a package having the first non-conforming condition into a first container and the second air jet ejecting a blast of air with sufficient force to deliver a package having the second non-conforming condition into a second container.

17. The method as defined in claim 12, wherein a detection sensor detects a foil condition of a package prior to detection of a surface condition of the package by at least one camera.

18. The method as defined in claim 17, wherein the at least one camera comprises three cameras operated to view different surfaces of the package.

19. The method as defined in claim 17, wherein the at least one camera comprises at least one video camera and a vision inspection data program analyzes signals from the at least one video camera to determine whether a package has a non-conforming surface condition.

20. The method as defined in claim 11, wherein the package comprises a cigarette package having graphics on one or more surfaces thereof.

21. An inspection apparatus for visually detecting non-conforming packages traveling along a conveyor path, the apparatus comprising:
   a conveyor transporting a plurality of identical packages along a conveyor path;
   a light source illuminating one of the packages at an inspection station along the conveyor path, the light source illuminating the package at the inspection station using a diffuse lighting source which includes a light reflector located in a reflector housing, at least one baffle located within the reflector housing, and at least one fiber optic lighting element, the at least one fiber optic lighting element delivering a pulsed beam of light that is dispersed by the at least one baffle and reflected by the light reflector while a package is located at a camera inspection position, and the light reflector illuminating the package with diffused light reflected from a surface of the light reflector;
   at least one camera outputting camera signals representing images of one or more surfaces of the package at the inspection station; and
   a controller operable to process data generated in response to the camera signals and identify a package having a non-conforming surface feature.

22. The apparatus as defined in claim 21, wherein the at least one fiber optic element comprises a plurality of fiber optic elements delivering pulsed beams of light into the reflector, the reflector including a flat white coating on a surface thereof facing the package to be inspected.

23. The apparatus as defined in claim 21, wherein the reflector housing surrounds a vertically oriented conveyor belt, the conveyor belt traveling over a vacuum chamber which applies a vacuum force to the belt to hold a package thereon as it travels through the inspection station.

24. The apparatus as defined in claim 23, wherein the at least one camera includes a video camera oriented to view a surface of a package facing away from the conveyor belt.

25. The apparatus as defined in claim 21, wherein the controller comprises a computer running a vision inspection program.

26. The apparatus as defined in claim 21, wherein the package is a cigarette package and the at least one camera inspects graphics and/or wrapping of the cigarette package.

27. The apparatus as defined in claim 21, further comprising a photo sensor which detects arrival of a package at the inspection station.

28. The apparatus as defined in claim 21, wherein the at least one camera comprises first, second and third video cameras oriented to inspect five different surfaces of the package.

29. The apparatus as defined in claim 28, wherein the first camera views a front surface of the package, the second camera views the top and one side surface of the package and the third camera views the bottom and the other side surface of the package.

30. A method of visually detecting non-conforming packages traveling along a conveyor path, the method comprising:
   transporting a plurality of identical packages along a conveyor path;
   illuminating one of the packages at an inspection station along the conveyor path, the package being illuminated at the inspection station using a diffuse lighting source which includes a light reflector located in a reflector housing, at least one baffle located within the reflector housing, and at least one fiber optic lighting element, the at least one fiber optic lighting element delivering a pulsed beam of light that is dispersed by the at least one baffle and reflected by the light reflector while a package is located at a camera inspection position, and the light reflector illuminating the package with diffused light reflected from a surface of the light reflector;
   outputting camera signals representing images of one or more surfaces of the package at the inspection station; and
   processing data generated in response to the camera signals so as to identify a package having a non-conforming surface feature.

31. The method as defined in claim 30, wherein the package is illuminated using a plurality of fiber optic elements delivering pulsed beams of light into the reflector, the reflector including a flat white coating on a surface thereof facing the package to be inspected.

32. The method defined in claim 30, wherein the reflector housing surrounds a vertically oriented conveyor belt, the method including using a conveyor belt traveling over a vacuum chamber to apply a vacuum force to the belt to hold a package thereon as it travels through the inspection station.

33. The method as defined in claim 32, wherein the camera signals are generated by a video camera oriented to view a surface of a package facing away from the conveyor belt.

34. The method as defined in claim 30, wherein camera signals are processed by a computer running a vision inspection program.

35. The method as defined in claim 30, wherein the package is a cigarette package and a video camera is used to inspect graphics and/or wrapping of the cigarette package.

36. The method as defined in claim 30, further comprising using a photo sensor to detect arrival of a package at the inspection station.

37. The method as defined in claim 30, wherein first, second and third video cameras are used to inspect five different surfaces of the package.

38. The method as defined in claim 37, wherein the first camera is used to view a front surface of the package, the second camera is used to view the top and one side surface of the package and the third camera is used to view the bottom and the other side surface of the package.

* * * * *